US009347319B2

(12) United States Patent
 Lai

(10) Patent No.: US 9,347,319 B2
(45) Date of Patent: May 24, 2016

(54) DENTAL HANDPIECE STRUCTURE

(71) Applicant: THUNDER TIGER CORPORATION, Taichung (TW)

(72) Inventor: Aling Lai, Taichung (TW)

(73) Assignee: THUNDER TIGER CORPORATION, TAICHUNG (TW)

( * ) Notice: Subject to any disclaimer, the term of this patent is extended or adjusted under 35 U.S.C. 154(b) by 701 days.

(21) Appl. No.: 13/753,831

(22) Filed: Jan. 30, 2013

(65) Prior Publication Data

US 2014/0212271 A1 Jul. 31, 2014

(51) Int. Cl.
 *A61C 1/05* (2006.01)
 *F01D 5/02* (2006.01)

(52) U.S. Cl.
 CPC .... *F01D 5/02* (2013.01); *A61C 1/05* (2013.01)

(58) Field of Classification Search
 None
 See application file for complete search history.

(56) References Cited

U.S. PATENT DOCUMENTS

| 3,408,043 | A | * | 10/1968 | Williams | F01D 15/067 |
| | | | | | 415/113 |
| 3,778,904 | A | * | 12/1973 | Melde | A61C 1/055 |
| | | | | | 433/120 |
| 3,952,416 | A | * | 4/1976 | Lingenhole | A61C 1/052 |
| | | | | | 433/104 |
| 4,146,964 | A | * | 4/1979 | Lares | A61C 1/05 |
| | | | | | 415/904 |
| 4,153,993 | A | * | 5/1979 | Kataoka | A61C 1/05 |
| | | | | | 310/90.5 |
| 5,538,425 | A | * | 7/1996 | Reeves | A61C 1/05 |
| | | | | | 433/126 |
| 5,542,846 | A | * | 8/1996 | Quinn | A61C 1/141 |
| | | | | | 279/106 |
| 5,567,154 | A | * | 10/1996 | Wohlgemuth | A61C 1/05 |
| | | | | | 415/904 |
| 2004/0018467 | A1 | * | 1/2004 | Tanaka | A61C 1/05 |
| | | | | | 433/132 |
| 2007/0087307 | A1 | * | 4/2007 | Flock | A61C 1/05 |
| | | | | | 433/132 |
| 2008/0070189 | A1 | * | 3/2008 | Turner | A61C 1/05 |
| | | | | | 433/132 |
| 2012/0308958 | A1 | | 12/2012 | Nakanishi | |

FOREIGN PATENT DOCUMENTS

WO 2012039329 3/2012

OTHER PUBLICATIONS http://www.kavo.com/Products/Dental-Instruments/Dental-Turbines/Spare-cartridges.aspx.

* cited by examiner

*Primary Examiner* — Nicholas Lucchesi
(74) *Attorney, Agent, or Firm* — Muncy, Geissler, Olds & Lowe, P.C.

(57) ABSTRACT

Disclosed is a dental handpiece structure including a head having a turbine chamber, a rotor installed in the turbine chamber and having a transmission shaft, and a transmission element composed of a plurality of turbine vanes. A high-pressure air entering into the turbine chamber can push each turbine vane to drive and rotate the rotor, and a breach is upwardly formed between two adjacent turbine vanes. A head cap is covered onto the turbine chamber, and a circular groove is formed at the head cap and between an end surface facing the turbine chamber and the transmission element, and the circular groove and each breach are arranged opposite to each other for collecting the high-pressure air guided out from each breach to enhance the cutting force of the dental handpiece.

7 Claims, 6 Drawing Sheets

DENTAL HANDPIECE STRUCTURE

BACKGROUND OF THE INVENTION

1. Field of the Invention

The present invention relates to a dental handpiece structure, and more particularly to the dental handpiece structure capable of improving the interference of airflow field in a turbine chamber, and providing a secondary impact on turbine vanes to increase the airflow field efficiency to enhance a cutting force.

2. Description of the Related Art

With reference to FIG. 6 for a conventional dental handpiece, the dental handpiece comprises a head 91, a turbine chamber 92 formed in the head 91 and having an upward opening, a rotor axially installed at the turbine chamber 92 and rotatable freely, and a screwing cap 94 locked onto the opening of the turbine chamber 92, wherein a burr 931 such as a molar knife or a drill is extended outwardly from an end of the rotor 93, and a transmission element 932 composed of a plurality of turbine vanes is formed at a middle section position of the rotor 93, so that when a high-pressure air enters into the turbine chamber 92, the gas can push the turbine vanes of the transmission element 932 to drive the rotor 93 to rotate in a circumferential direction of the rotor 93.

In the actual use of the conventional dental hand-piece, the high-pressure air is guided towards the breach between two adjacent turbine vanes to the outside, after the high-pressure air entering into the turbine chamber 92 pushes the turbine vanes of the transmission element 932. Since an end surface of the screwing cap 94 facing the turbine chamber 92 is substantially in a flat shape without any design of guiding and collecting the high-pressure air, therefore the upwardly guided high-pressure air may create a turbulence (as indicated by the arrow in the figure) easily when the gas impacts the end surface at the bottom of the screwing cap 94, and an interference of the airflow field in the turbine chamber 92 is formed to result in the disadvantages of an increased rotating resistance and a decreased torque. In addition, the gas in the turbine chamber 92 of the conventional dental handpiece may be discharged quickly, so that the effects of producing a secondary impact of the turbine vanes by the high-pressure air or improving the work efficiency of the airflow field cannot be achieved.

SUMMARY OF THE INVENTION

Therefore, it is a primary objective of the present invention to overcome the problems by providing a dental handpiece structure capable of improving the interference of an airflow field in a turbine chamber effectively.

The secondary objective of the present invention is to provide a dental handpiece structure that provides a secondary impact of the turbine vanes to improve the work efficiency of the airflow field and enhance the cutting force of the dental hand-piece.

To achieve the aforementioned objective, the present invention provides a dental handpiece structure, comprising:

a head, having a turbine chamber formed therein, an opening formed at the top of the turbine chamber, a through hole formed at the bottom of the turbine chamber, and an air intake hole and an air vent hole formed on an inner wall of the turbine chamber;

a rotor, installed in the turbine chamber, and having a transmission shaft, and a transmission element installed at the external periphery of the transmission shaft, and the transmission element being formed by sequentially arranging a plurality of turbine vanes in a circle, and a high-pressure air entering into the turbine chamber through the air intake hole being capable of pushing each turbine vane of the transmission element to drive and rotate the rotor, and a breach being formed between two adjacent turbine vanes of the transmission element and aligned towards the opening, such that the high-pressure air pushing the transmission element is guided out from each breach; and a head cap, covered onto the opening of the turbine chamber, and having a circular groove formed in a circumferential direction of the head cap and between an end surface of the turbine chamber and the transmission element and disposed opposite to each the breach, for collecting the high-pressure air guided through each breach.

Preferably, the circular groove is concavely formed in a circumferential direction on an end surface of the head cap facing the turbine chamber, and the bottom of the circular groove is substantially in a concave arc shape.

Further, the transmission element has a block edge disposed around an end of the transmission element which is away from the opening, and the head cap has a press button protruded towards a direction away from the circular groove, and one or more notches formed at the periphery of the press button.

In addition, the air vent hole has a sunken section extended in a rotating direction of the rotor, and a circular arc shaped guide slot concavely formed at an end edge of each turbine vane of the transmission element and aligned towards the opening, and the sunken section of the air vent hole and the guide slot of each turbine vane are arranged opposite with one another and disposed at the same horizontal height position.

DETAILED DESCRIPTION OF THE PREFERRED EMBODIMENTS

The technical content of the present invention will become apparent with the detailed description of preferred embodiments and the illustration of related drawings as follows. It is noteworthy that same numerals used in the following preferred embodiments and related drawings represent respective elements of the invention.

Figure 1:
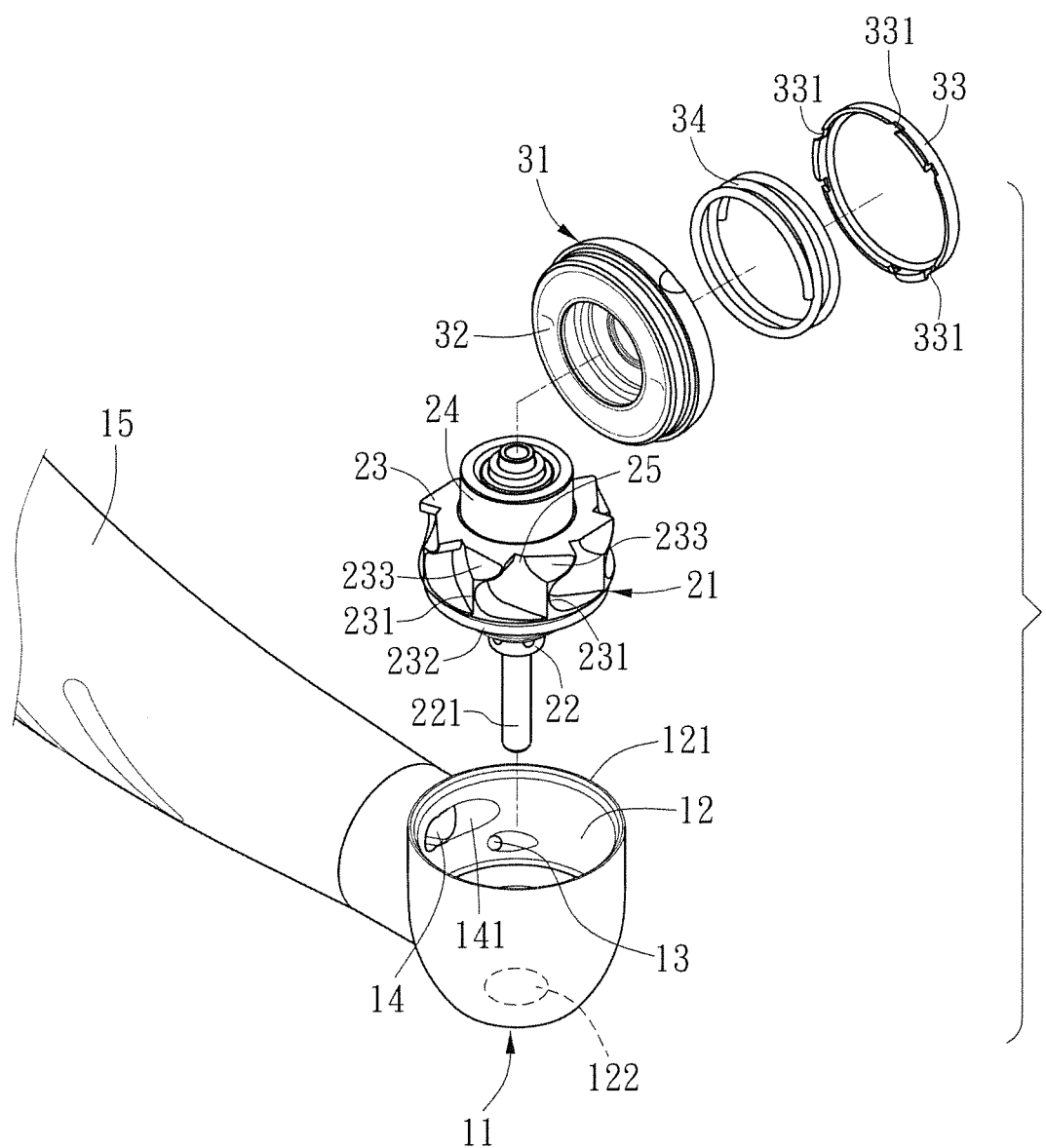
FIG. 1 is an exploded view of the present invention.
Figure 2:
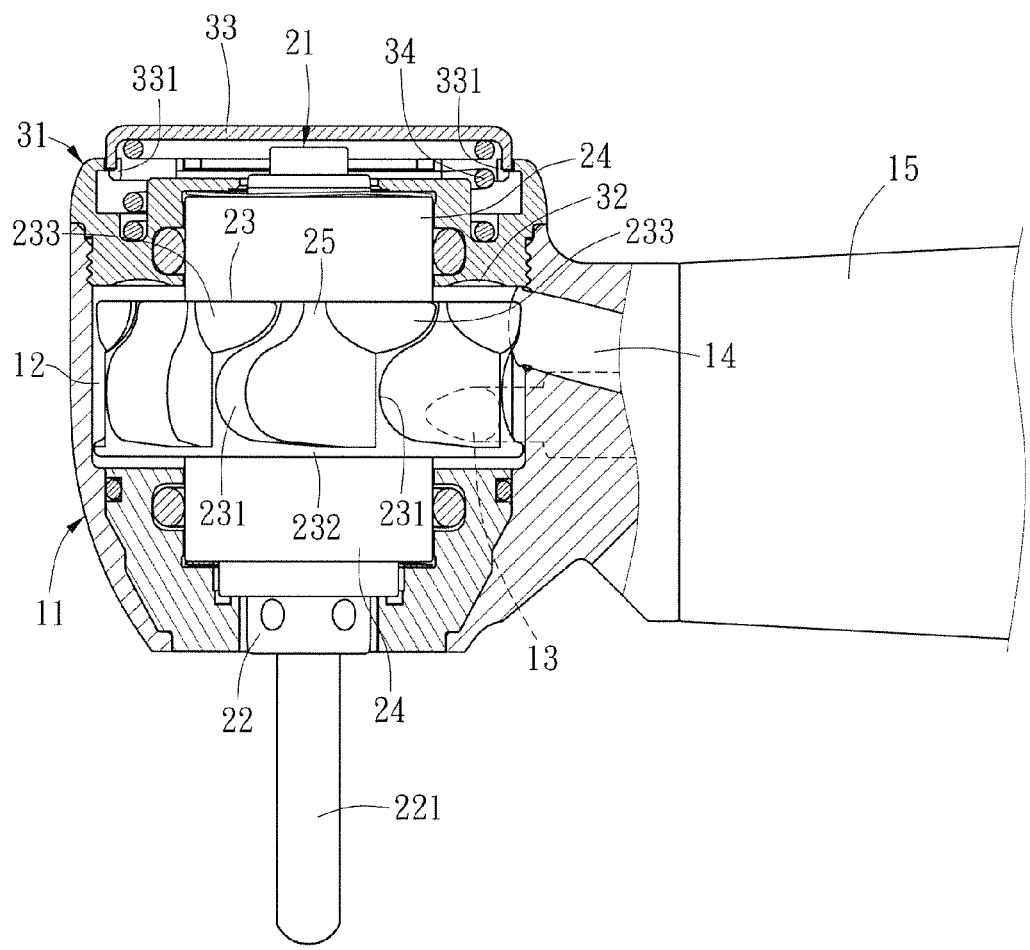
FIG. 2 is a cross-sectional view of an assembly of the present invention.

With reference to FIGS. 1 and 2 for a dental handpiece structure of the present invention, the dental handpiece structure comprises a head 11, a rotor 21 and a head cap 31.

The head 11 has a turbine chamber 12 formed therein, an opening 121 formed at the top of the turbine chamber 12, a through hole 122 formed at the bottom of the turbine chamber 12, an air intake hole 13 and an air vent hole 14 formed on an inner wall of the turbine chamber 12, and a grip 15 extended outwardly from a rear end of the head 11 and provided for gripping the head 11 by hand.

The rotor 21 is axially installed in the turbine chamber 12 through the opening 121 of the turbine chamber 11, and the rotor 21 has a transmission shaft 22 and a transmission element 23, wherein a burr 221 is installed at an end of the transmission shaft 22, passed through the through hole 122, and protruded to the outside of the turbine chamber 12, and the burr 221 that can be a molar knife or a drill, and the transmission element 23 is formed by sequentially arranging a plurality of turbine vanes 231 around the external periphery of the rotor 21. In addition, a bearing 24 is sheathed separately at the top and bottom of the transmission element 23 respectively, and the transmission element 23 has a block edge 232 formed around the transmission element 23 and away from the bottom of the opening 121, and a breach 25 is formed between two adjacent turbine vanes 231 of the transmission element 23 and facing the opening 121. The high-pressure air entering from the air intake hole 13 into the turbine chamber 12 can push each turbine vane 231 of the transmission element 23 to drive and rotate the rotor 21, and a circular arc shaped guide slot 233 is concavely formed at an end edge of each turbine vane 231 of the transmission element 23 and facing the opening 121, and the air vent hole 14 has a sunken section 141 extended in a rotating direction of the rotor 21, and the sunken section 141 of the air vent hole 14 and the guide slot 233 formed on each turbine vane 231 are disposed opposite to each other and at the same horizontal height position.

The head cap 31 is covered onto the opening 121 of the turbine chamber 12, and the head cap 31 has a circular groove 32 formed between an end surface of the turbine chamber 12 and the transmission element 23 and along a circumferential direction of the head cap 31, and the circular groove 32 and each the breach 25 are arranged opposite to each other for collecting the high-pressure air guided through each breach 25. In this preferred embodiment, the circular groove 32 is concavely formed in a circumferential direction of the head cap 31 and aligned towards an end surface of the turbine chamber 12, and the circular groove 32 has a bottom substantially in a concave arc shape, and the head cap 31 has a press button 33 installed thereon, an elastic element 34 clamped between the press button 33 and the head cap 31 such that the press button 33 can be protruded in a direction away from the circular groove 32, and a plurality of notches 331 formed at the periphery of the press button 33.

Figure 3:
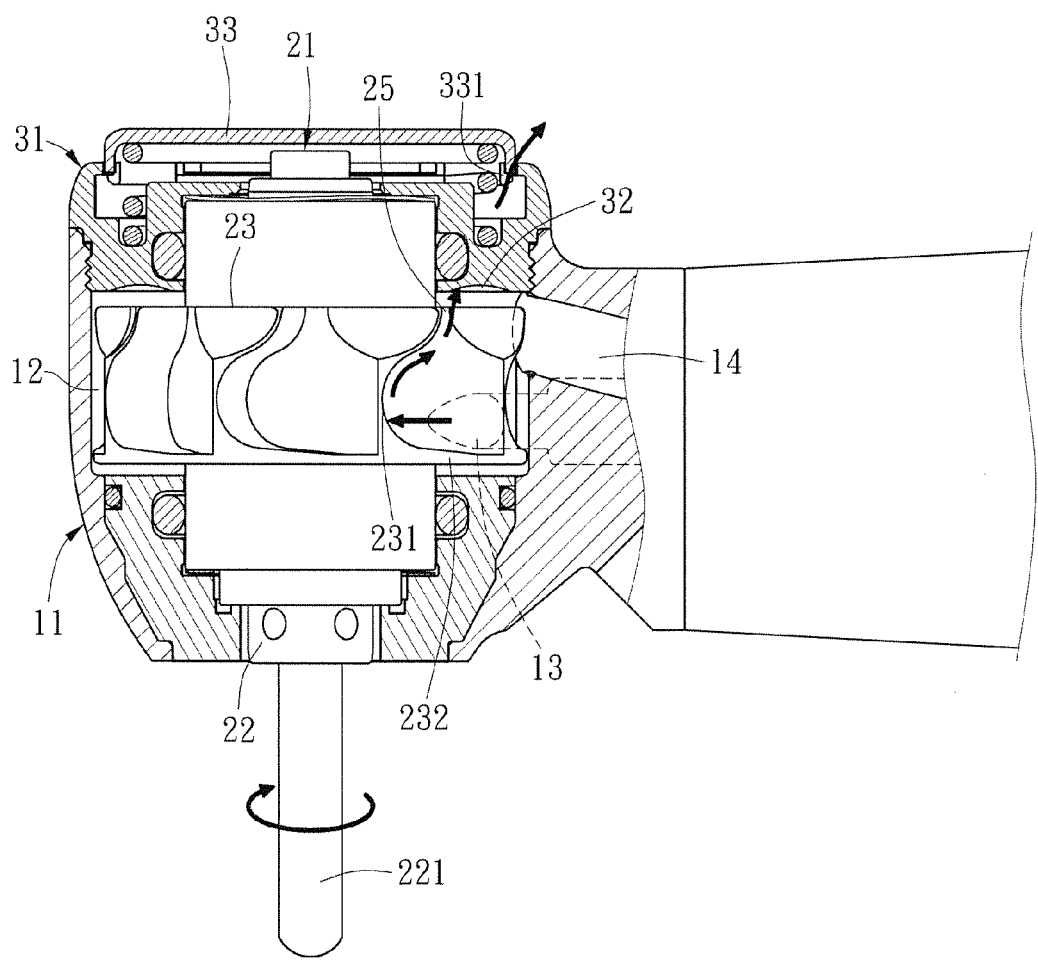
FIG. 3 is a schematic view of a using status of the present invention, showing the status of an airflow when a high-pressure air is pumped into a turbine chamber.

In an actual use of the structure of the present invention as shown in FIG. 3, a high-pressure air is pumped into the turbine chamber 12 through the air intake hole 13, so that the high-pressure air can push each turbine vane 231 of the transmission element 23 to drive the rotor 21 and link the burr 221 to rotate. Since the bottom of the transmission element 23 is blocked by the block edge 232, therefore the high-pressure air can be guided upwardly along each turbine vane 231 through the breach 25 between the walls of the turbine vanes 231 after the high-pressure air pushes each turbine vane 231 of the transmission element 231, so that the high-pressure air guided through each breach 25 can be collected by the circular groove 32 disposed opposite to each breach 25. Since the bottom of the circular groove 32 is in a circular arc shape, air can flow smoothly along the circular groove 32 to reduce the turbulence of the high-pressure air effectively, and a small portion of the high-pressure air in the head cap 31 can be discharged to the outside through the notch 331 of the press button 33, so as to prevent the high-pressure air from flowing back into the turbine chamber 12 and assure that airflow field of the turbine chamber 12 will not be affected.

Figure 4:
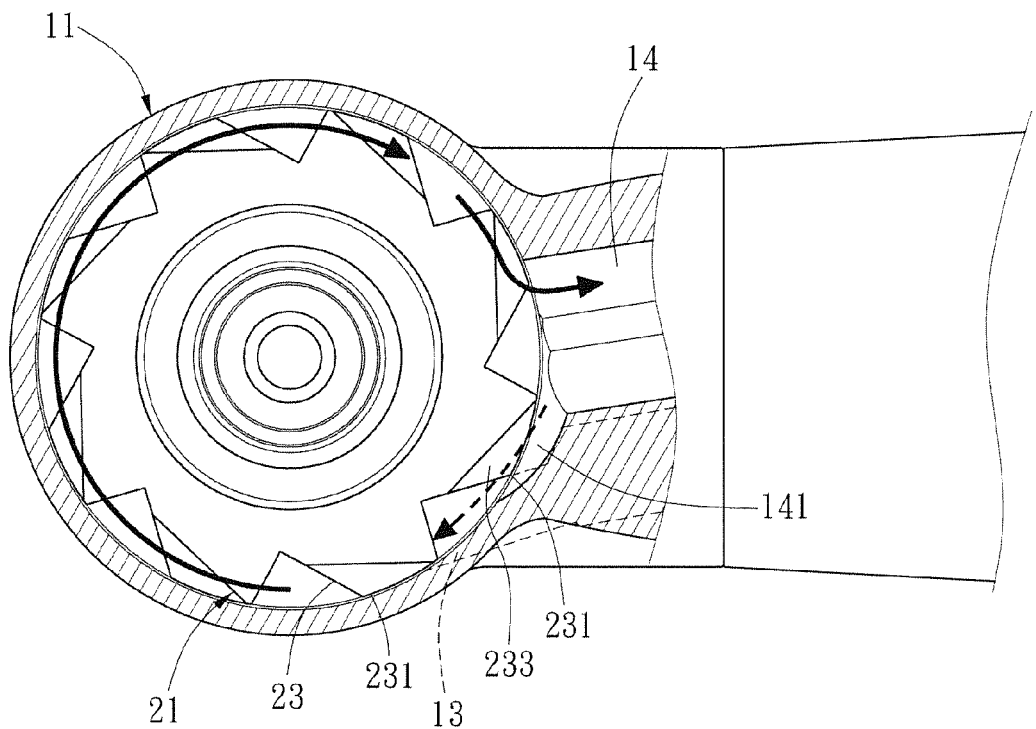
FIG. 4 is a schematic view of a using status of the present invention, showing the status of an airflow when a high-pressure air guided into a circular groove flows towards the rear side along the rotating direction of a rotor.
Figure 5:
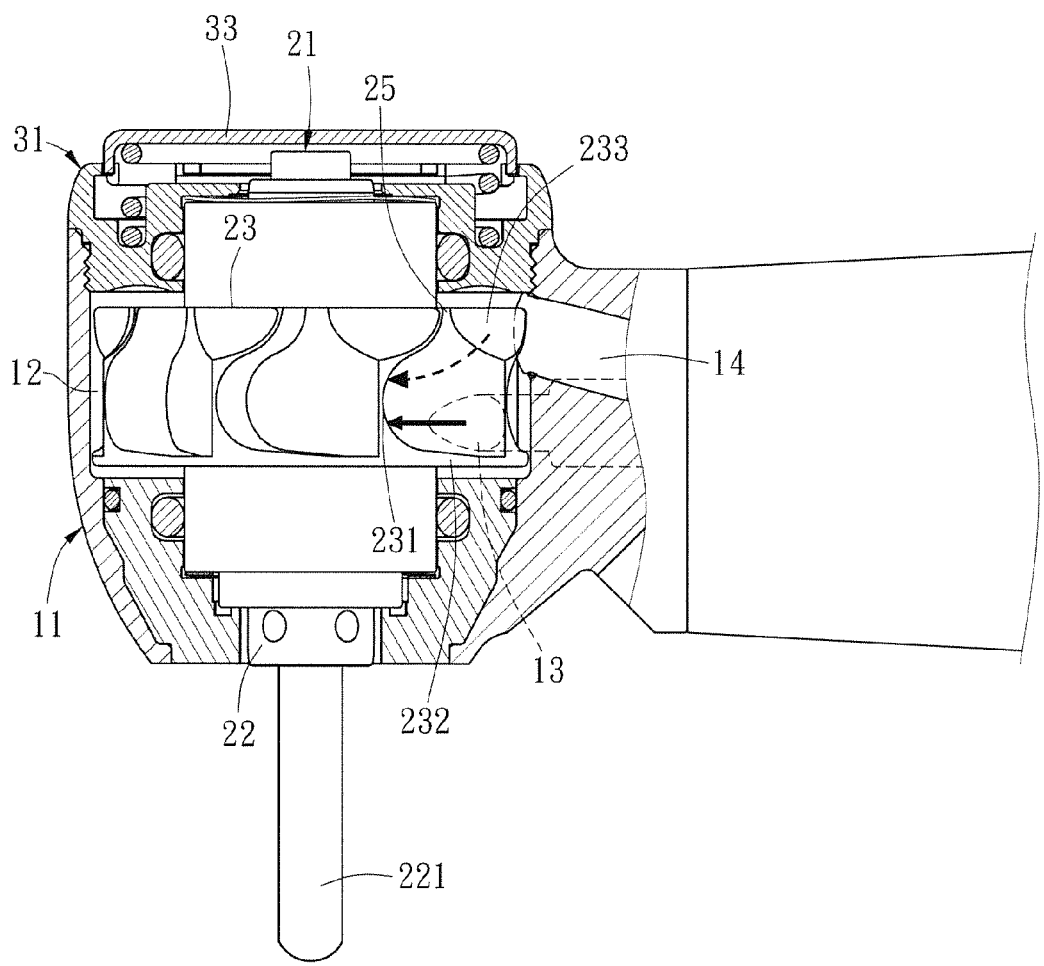
FIG. 5 is a schematic view of a using status of the present invention, showing the status of an airflow when air is guided through a guide slot into each turbine vane.
Figure 6:
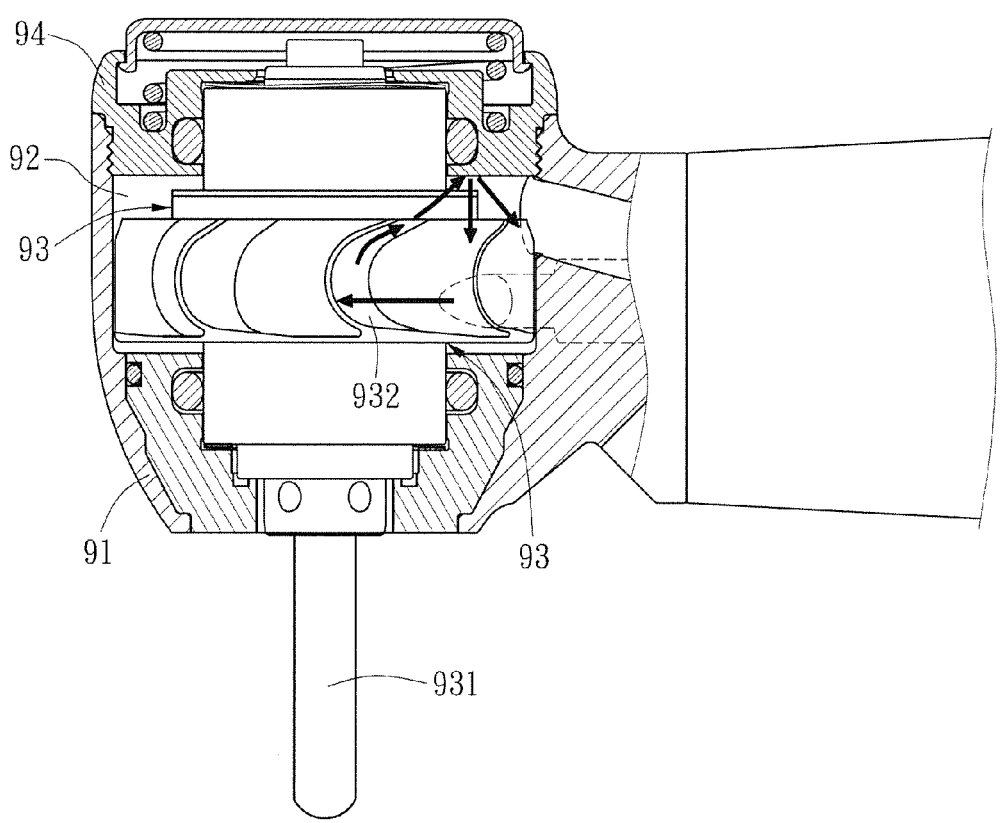
FIG. 6 is a schematic view of a conventional dental hand-piece structure.

With reference to FIGS. 4 and 5, the high-pressure air guided into the circular groove 32 flows towards the rear side along a rotating direction of the rotor 21, and a portion of the high-pressure air entering into the air vent hole 14 is guided to the outside, and the other portion of the high-pressure air (as indicated by the dotted line in the figure) is guided by the sunken section 141 of the concave arc shaped air vent hole 14 to flow from the guide slot 233 at the same horizontal height position of the sunken section 141 into the place between each turbine vane 231 of the transmission element 23, so as to achieve the effect of a secondary impact of the turbine vanes 231. Therefore, the present invention can increase the work efficiency of airflow field of the turbine chamber, so as to enhance the cutting force of the dental handpiece cutting.

What is claimed is:

1. A dental handpiece structure, comprising:
    a head, having a turbine chamber formed therein, an opening formed at the top of the turbine chamber, a through hole formed at the bottom of the turbine chamber, and an air intake hole and an air vent hole formed on an inner wall of the turbine chamber;
    a rotor, installed in the turbine chamber, and having a transmission shaft, and a transmission element installed at the external periphery of the transmission shaft, and the transmission element having a plurality of turbine vanes sequentially arranged in a circle, such that when a high-pressure air enters into the turbine chamber through the air intake hole, each turbine vane of the transmission element is pushed to drive and rotate the rotor, and a breach being formed between two adjacent turbine vanes of the transmission element and aligned towards the opening, such that the high-pressure air pushing the transmission element is guided out from each breach; and
    a head cap, covered onto the opening of the turbine chamber, and having a circular groove formed in a circumferential direction of the head cap and between an end surface of the turbine chamber and the transmission element and disposed opposite to each breach, for collecting the high-pressure air guided through each breach.

2. The dental handpiece structure of claim 1, wherein the circular groove has a bottom substantially in a concave arc shape.

3. The dental handpiece structure of claim 1, wherein the circular groove is concavely formed along a circumferential direction at an end surface of the head cap facing the turbine chamber.

4. The dental handpiece structure of claim 3, wherein the circular groove has a bottom substantially in a concave arc shape.

5. The dental handpiece structure of claim 1, wherein the transmission element has a block edge disposed around an end of the transmission element which is away from the opening.

6. The dental handpiece structure of claim 1, wherein the head cap has a press button protruded towards a direction away from the circular groove, and one or more notches formed at the periphery of the press button.

7. The dental handpiece structure of claim 1, wherein the air vent hole has a sunken section extended in a rotating direction of the rotor, and a circular arc shaped guide slot concavely formed at an end edge of each turbine vane of the transmission element and aligned towards the opening, and the sunken section of the air vent hole and the guide slot of each turbine vane are arranged opposite with one another and disposed at the same horizontal height position.

* * * * *